(12) United States Patent
Nagase et al.

(10) Patent No.: US 9,265,421 B2
(45) Date of Patent: Feb. 23, 2016

(54) MEDICAL MONITORING SYSTEM

(71) Applicant: NIHON KOHDEN CORPORATION, Shinjuku-ku, Tokyo (JP)

(72) Inventors: Kazuya Nagase, Tokyo (JP); Hiromitsu Kasuya, Tokyo (JP); Hiroyuki Taniguchi, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 121 days.

(21) Appl. No.: 14/180,782

(22) Filed: Feb. 14, 2014

(65) Prior Publication Data

US 2014/0225746 A1 Aug. 14, 2014

(30) Foreign Application Priority Data

Feb. 14, 2013 (JP) .................. 2013-026840

(51) Int. Cl.
  *G08B 19/00* (2006.01)
  *A61B 5/00* (2006.01)
  *G06F 19/00* (2011.01)
(52) U.S. Cl.
  CPC .............. *A61B 5/002* (2013.01); *A61B 5/0002* (2013.01); *A61B 5/742* (2013.01); *A61B 5/746* (2013.01); *A61B 5/7445* (2013.01); *G06F 19/3418* (2013.01)
(58) Field of Classification Search
  CPC .... A61B 5/0002; A61B 5/024; A61B 5/0013; A61B 5/0205; A61B 5/145; A61B 5/118; A61B 5/747; A61B 5/1072; A61B 2560/0271; A61B 2560/0443; G08B 21/0294
  See application file for complete search history.

(56) References Cited

U.S. PATENT DOCUMENTS

| 5,003,984 | A | 4/1991 | Muraki et al. |
| 6,057,758 | A * | 5/2000 | Dempsey et al. ........ 340/539.12 |
| 2003/0126593 | A1* | 7/2003 | Mault ............................ 725/10 |
| 2005/0151640 | A1 | 7/2005 | Hastings |
| 2007/0180140 | A1 | 8/2007 | Welch et al. |
| 2011/0105854 | A1* | 5/2011 | Kiani et al. ................... 600/300 |

(Continued)

FOREIGN PATENT DOCUMENTS

| JP | 07-027741 Y2 | 6/1995 |
| WO | 2007/065015 A2 | 6/2007 |

OTHER PUBLICATIONS

EP Search Report dated May 27, 2014, issued by the European Patent Office in counterpart European Application No. 14155133.3.

*Primary Examiner* — Kerri McNally
*Assistant Examiner* — Renee Dorsey
(74) *Attorney, Agent, or Firm* — Sughrue Mion, PLLC

(57) ABSTRACT

A medical monitoring system includes: a plurality of biological information displaying devices connected to a network; and a portable terminal which can wirelessly communicate with the biological information displaying devices. The plurality of biological information displaying devices includes a first device and a second device. When a value of biological information is larger or smaller than a preset threshold, the first device transmits alarm information. In case where the first device transmits the alarm information, a receiving unit of the portable terminal receives the alarm information, and a transmitting unit of the portable terminal wirelessly transmits the received alarm information to the second device, and the second device receives the biological information through the network and the biological information is displayed on the second device.

13 Claims, 4 Drawing Sheets

(56) References Cited

U.S. PATENT DOCUMENTS

| | | | |
|---|---|---|---|
| 2011/0148622 A1* | 6/2011 | Judy et al. | 340/539.12 |
| 2012/0127103 A1 | 5/2012 | Qualey et al. | |
| 2012/0203078 A1* | 8/2012 | Sze et al. | 600/301 |
| 2014/0135603 A1* | 5/2014 | Boyer et al. | 600/324 |
| 2014/0184408 A1* | 7/2014 | Herbst et al. | 340/539.12 |

\* cited by examiner

MEDICAL MONITORING SYSTEM

CROSS-REFERENCE TO RELATED APPLICATION(S)

This application is based upon and claims the benefit of priority from prior Japanese patent application No. 2013-026840, filed on Feb. 14, 2013, the entire contents of which are incorporated herein by reference.

BACKGROUND

The presently disclosed subject matter relates to a medical monitoring system for displaying biological information of a patient on a display screen.

In order to monitor the condition of a patient in a medical institution, a biological information monitor (bedside monitor) which is placed at the side of a bed is used. When biological information of a patient acquired from a bedside monitor deviates from a predetermined range, the bedside monitor generates an audible alarm to inform of this situation. A procedure on the patient from whom the audible alarm is generated must be conducted rapidly and correctly. However, the determination on whether biological information deviates from the range or not is performed in an automatic manner, and therefore a situation where the audible alarm is erroneously generated by a cause other than the symptom of the patient often occurs. Therefore, a medical person is variously swayed by audible alarms. When audible alarms from a plurality of patients are simultaneously generated, there is a possibility that procedures cannot be conducted rapidly and correctly.

In order to comply with the above, for example, JP-UM-B-07-027741 discloses a portable wireless call receiver having a function of displaying a waveform from which it is possible to correctly determine whether a transmitted patient alarm (audible alarm) is true or false. According to the disclosure, in a portable wireless call receiver which is one type of pager to be carried by a medical person (a doctor or a nurse), a waveform of an electrocardiographic signal, which is included in received biological information signals of the patient and which is generated at least at the time when the patient alarm is issued, is displayed on a displaying section. Therefore, it is possible to determine the condition of the patient, and also whether the patient alarm is true or false.

In the portable wireless call receiver having a function of displaying a waveform disclosed in JP-UM-B-07-027741, the receiver has a portable size, and hence also the displaying section has a small size. In the case where a plurality of sets of biological information related to the patient are to be displayed on the displaying section, therefore, it is difficult to clearly display the whole contents of the information. In order to determine more clearly the condition of the patient from whom the patient alarm is generated, consequently, the medical person must move to the bedside monitor for the patient.

In the case where a plurality of sets of biological information of the patient from whom the patient alarm is generated are to be clearly displayed on a displaying section of a portable receiver, the receiver itself including the displaying section is required to be increased in size and enhanced in performance. This causes the production cost to be increased.

SUMMARY

The presently disclosed subject matter may provide a medical monitoring system in which the condition of a patient can be determined rapidly and correctly without increasing the size and enhancing the performance of a portable receiver.

The medical monitoring system may comprise: a plurality of biological information displaying devices which are connected to a network; and a portable terminal which can wirelessly communicate with the plurality of biological information displaying devices, wherein the plurality of biological information displaying devices includes a first device and a second device, biological information of a first patient is input to the first device, when a value of first biological information included in the biological information of the first patient is larger or smaller than a preset threshold, the first device transmits alarm information, the portable terminal includes: a receiving unit which can receive the alarm information from the first device; and a transmitting unit which can wirelessly transmit the received alarm information to the second device, and, in case where the first device transmits the alarm information, the receiving unit of the portable terminal receives the alarm information, and the transmitting unit of the portable terminal wirelessly transmits the received alarm information to the second device, and the second device receives the biological information of the first patient through the network and the biological information of the first patient is displayed on the second device.

The first device may transmit the first biological information the value of which is larger or smaller than the threshold, in addition to the alarm information. In case where the first device transmits the alarm information and the first biological information, the receiving unit of the portable terminal receives the alarm information and the first biological information, and the transmitting unit of the portable terminal wirelessly transmits the received alarm information and the received first biological information to the second device, and the alarm information and the first biological information are displayed on the second device.

Biological information of a second patient may be displayed on the second device.

The biological information of the first patient is displayed overlappingly with a part of an image displayed on the second device.

The alarm information and the first biological information are displayed overlappingly with a part of an image displayed on the second device.

In case where the receiving unit of the portable terminal receives two or more of alarm information, the transmitting unit of the portable terminal wirelessly transmits alarm information which is selected by an operator.

In case where two or more of alarm information are selected by the operator and the transmitting unit of the portable terminal wirelessly transmits the selected two or more of alarm information, biological information input to two or more biological information displaying devices which transmit the selected two or more of alarm information is displayed in a split manner or overlappingly with a part of an image displayed on the second device.

The second device may receive the biological information of the first patient through the network based on the alarm information.

DETAILED DESCRIPTION OF EXEMPLARY EMBODIMENTS

Hereinafter, embodiments of the medical monitoring system of the presently disclosed subject matter will be described with reference to the accompanying drawings.

First Embodiment

Figure 1:
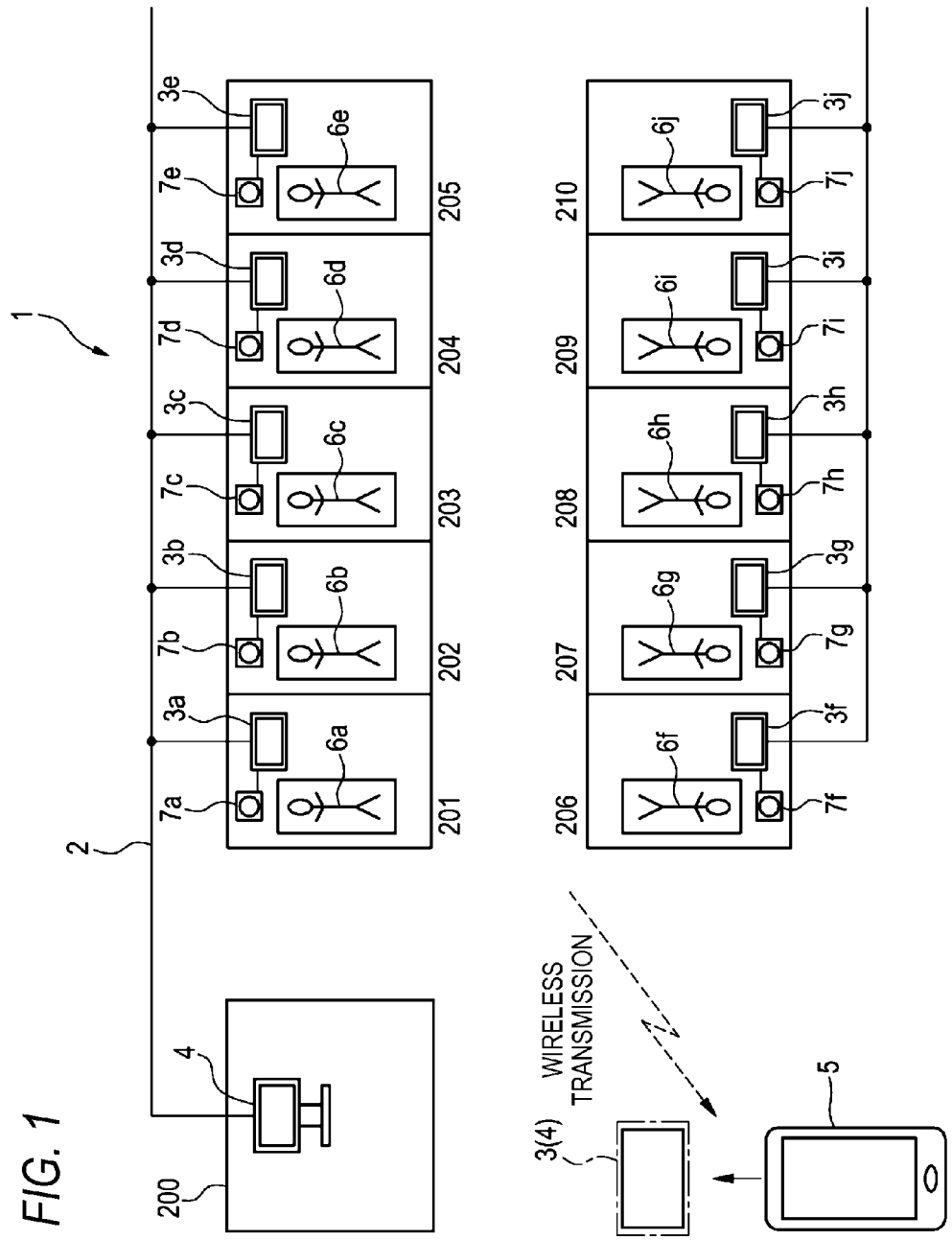
FIG. 1 is a diagram illustrating the configuration of the medical monitoring system of the presently disclosed subject matter.

FIG. 1 is a diagram schematically illustrating the configuration of the medical monitoring system 1. The medical monitoring system 1 may include: a plurality of biological information displaying devices 3 (bedside monitors 3a, 3b, 3c, . . . , 3j) which are connected to each other via a wired or wireless network 2; a central monitor 4 similarly connected to the network 2; and a portable terminal 5 which can wirelessly communicate with the monitors.

FIG. 1 illustrates one floor (for example, a surgical floor) of a certain hospital. The bedside monitors 3a, 3b, 3c, . . . , 3j are disposed inpatient rooms Nos. 201, 202, 203, . . . , 210, respectively, and the central monitor 4 is disposed in a nurses' station 200.

The bedside monitors 3a, 3b, 3c, . . . , 3j can connect to sensors for acquiring biological information of parameters such as the heart rate, the blood pressure, the oxygen saturation, and the like. As required, the sensors are attached to patients 6a, 6b, 6c, . . . , 6j in order to measure biological information.

The bedside monitors 3a, 3b, 3c, . . . , 3j can further connect to cameras 7a, 7b, 7c, . . . , 7j for taking pictures of the patients in the patient rooms, respectively. The cameras may be usual video cameras and Web cameras which can transfer real time images.

The portable terminal 5 is carried by a medical person, and can wirelessly communicate with the bedside monitors 3a, 3b, 3c, . . . , 3j and the central monitor 4.

Figure 2:
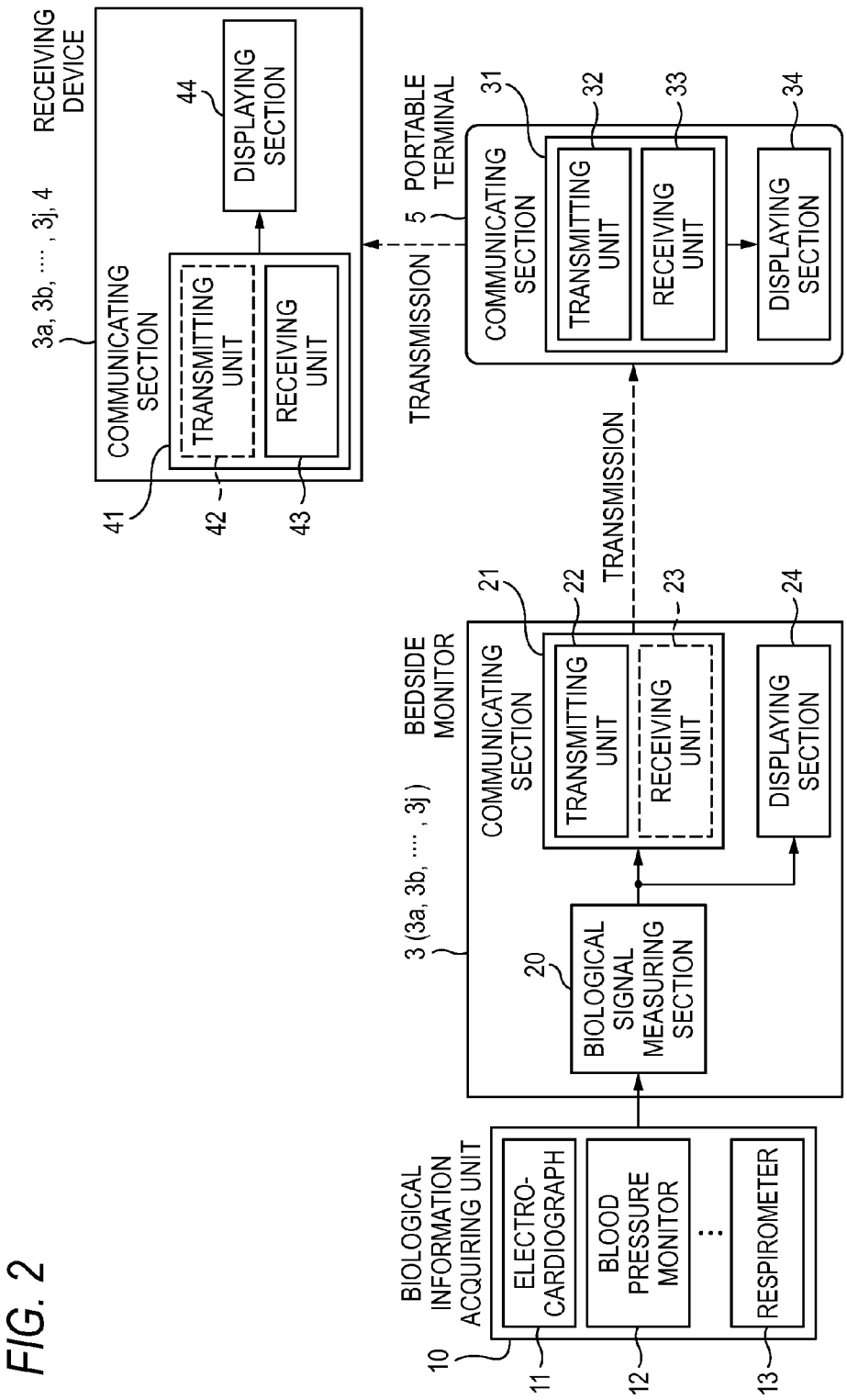
FIG. 2 is a block diagram illustrating an example of the functional configuration of the medical monitoring system.

FIG. 2 schematically illustrates the functional configuration of the medical monitoring system 1.

Each of the bedside monitors 3 is a device which, when it is determined that an abnormality occurs in biological information of the patient under measurement, transmits alarm information, and may include: a biological signal measuring section 20: a communicating section 21 including a transmitting unit 22 and a receiving unit 23; and a displaying section (display screen) 24.

The biological signal measuring section 20 measures the value of acquired biological information, and determines whether an abnormality exists or not. Specifically, the determination is performed by a comparing and determining unit which is disposed in the biological signal measuring section 20. A measurement value (a numerical value, a waveform, or the like) measured from the patient is compared with a predetermined threshold, and, if the measurement value exceeds the threshold (is larger or smaller than the threshold), it is determined that an abnormality occurs in the patient. If it is determined that an abnormality occurs, the biological signal measuring section 20 outputs alarm information informing of the situation and its contents, to the communicating section 21.

The transmitting unit 22 of the communicating section 21 is a communicating unit which wirelessly transmits the alarm information output from the biological signal measuring section 20, to the portable terminal 5. The receiving unit 23 of the communicating section 21 is a communicating unit which receives a signal which is transmitted from the portable terminal 5 by short-range wireless communication.

The alarm information is wirelessly transmitted from the bedside monitor which generates the alarm, to the portable terminal 5 through the transmitting unit 22. The alarm information is further transmitted from the bedside monitor to the central monitor 4 through the network 2 (see FIG. 1). At this time, information indicating that an alarm occurs may be displayed by using an alarm displaying unit (not shown) which is disposed in the bedside monitor. For example, the information may be visibly displayed by turning on or blinking an alarm indicator disposed in the bedside monitor, or an audible alarm may be output from a speaker.

The displaying section 24 is a display screen on which biological information of the patient under measurement is displayed, and may be configured by, for example, an LCD.

Biological information acquiring units 10 for measuring biological information of the respective patients are connected to the respective bedside monitors 3. Specific examples of the biological information acquiring units 10 may be various sensors such as an electrocardiograph 11, a blood pressure monitor 12, and a respirometer 13. Sets of biological information acquired by the biological information acquiring units 10 are supplied to the biological signal measuring sections 20 of the bedside monitors 3, respectively. Although not illustrated, each of the respective bedside monitors 3 may include a storing unit (memory) for holding the acquired biological information.

The portable terminal 5 is a terminal which is to be carried by the medical person in order to transmit and receive alarm information, and may include: a communicating section 31 including transmitting and receiving units 32, 33 for performing wireless communication; and a displaying section 34 which displays transmitted information. The portable terminal 5 may be a smart phone, an in-hospital PHS phone (medical PHS phone) and a portable telephone which is connectable via a Wi-Fi network.

The receiving unit 33 of the communicating section 31 is a communicating unit which receives alarm information that is wirelessly transmitted from each the bedside monitors 3. The transmitting unit 32 of the communicating section 31 is a communicating unit which, by short-range wireless transmission, transmits alarm information received from the bedside monitor 3 to an arbitrary receiving device (the bedside monitors 3a, 3b, 3c, . . . , 3j or the central monitor 4) that is designated by the medical person.

As a communicating unit which performs short-range wireless transmission, for example, an NFC (Near Field communications) may be used. When NFC compliant devices are moved closer to each other, i.e., when the portable terminal 5 is held against an arbitrary receiving device (the bedside monitors 3a, 3b, 3c, . . . , 3j or the central monitor 4), they are mutually authenticated, and the alarm information of the portable terminal 5 can be transmitted to the arbitrary receiving device.

The displaying section 34 is a display screen on which alarm information that is wirelessly transmitted from the bedside monitor 3 is displayed, and may be configured by, for example, an LCD.

When the portable terminal 5 receives alarm information, an incoming sound (incoming vibrations) is output, and alarm information, which includes information indicating that abnormality occurs in the biological information of the patient, and information such as the patient ID, the patient room No., the name of the patient, and the like, is displayed on the displaying section 34.

To the portable terminal 5 of each medical person, alarm information of patients for whom the medical person is responsible is transmitted. It is assumed that a medical person A is working in a department of surgery, the patients 6a, 6b, 6c, ..., 6j undergo treatment on the surgical floor shown in FIG. 1, and alarm information of one of the patients who are among the above-described patients and for whom the medical person A is responsible is transmitted to the portable terminal 5 of the medical person A. In this case, the medical person A is requested to register the portable terminal 5 of the medical person A into the bedside monitors disposed in the room of the concerned patients. In the case where the patient B for whom the medical person A is responsible receives treatment in a patient room on another floor (for example, internal medicine), when the portable terminal 5 carried by the medical person A is registered into the bedside monitor disposed in the patient room, alarm information of the patient B is transmitted to the portable terminal of the medical person A.

The receiving device is any monitor which is an arbitrarily one of the bedside monitors 3a, 3b, 3c, ..., 3j and the central monitor 4 designated by the medical person in order to transmit alarm information, and includes a communicating section 41 and a displaying section 44.

A receiving unit 43 of the communicating section 41 is a communicating unit which receives alarm information that is transmitted from the portable terminal 5 by short-range wireless communication. A transmitting unit 42 is a communicating unit for transmitting the alarm information to the portable terminal 5.

The displaying section 44 is a display screen on which biological information of the patient from whom the alarm information is generated is displayed. The biological information of the patient from whom the alarm information is generated is received via the network 2 based on the alarm information transmitted from the portable terminal 5. The displaying section 44 may be configured by, for example, an LCD.

According to the configuration, the medical person receives alarm information which is wirelessly transmitted from the bedside monitor 3a, 3b, 3c, ..., 3j that detects abnormality in biological information of the patient, through the portable terminal 5 carried by the medical person. Then, the medical person arbitrarily designates one of the bedside monitors 3a, 3b, 3c, ..., 3j and central monitor 4 connected to the network 2, and transmits the received alarm information by short-range wireless transmission to the designated monitor through the portable terminal 5. As a result, biological information which is related to the patient from whom alarm information is generated, and which is received via the network 2 based on the patient ID and the like included in the alarm information is displayed on the display screen of the designated one of the bedside monitors 3a, 3b, 3c, ..., 3j and central monitor 4 to which the alarm information is transmitted. At this time, for example, transmission of alarm information to the designated monitor can be realized by a simple operation in which the portable terminal 5 is held against (moved closer to) the designated monitor.

Specifically, it is assumed that, for example, the medical person A is in the vicinity of the patient 6a in the patient room No. 201 shown in FIG. 1 in the course of rounds. In the case where abnormality occurs in biological information of the patient 6j at this time, alarm information informing of this is wirelessly transmitted from the bedside monitor 3j to the portable terminal 5 of the medical person A. The portable terminal 5 of the medical person A generates an incoming sound (incoming vibrations) to inform that alarm information is received. Moreover, information such as "Patient ID: xxxxxxx", the patient room "No. 210", the name of the patient "KOHDEN Taro" of the patient 6j is displayed together with a message "ABNORMALITY OCCURS IN BIOLOGICAL INFORMATION" on the display screen of the portable terminal 5.

In this case, the medical person A causes the portable terminal 5 to perform short-range wireless communication on the bedside monitors connected to the network 2, for example, the bedside monitor 3a which is nearest (performs a simple operation in which the portable terminal 5 is moved closer to the bedside monitor 3a), and the received alarm information (such as "Patient ID: xxxxxxx") is transmitted. As a result, the biological information of the patient 6j from whom alarm information is generated, and a camera image of the patient 6j can be displayed on the display screen of the bedside monitor 3a.

As described above, without moving from the patient room where the medical person is making the rounds, the medical person can check biological information of a patient from whom alarm information is generated, and who is in a remote patient room, through the monitor (nearest monitor) disposed in the patient room where the medical person is making the rounds.

This is similarly applicable independent of the location of the medical person. It is not required that, each time when alarm information is received, the medical person moves to the patient room of the patient from whom alarm information is generated. The medical person is requested only to perform short-range wireless communication using the portable terminal 5 on the bedside monitor 3a, 3b, 3c, ..., 3j or central monitor 4 which is nearest.

Each time when abnormality is detected in biological information which is measured in the bedside monitors 3a, 3b, 3c, ..., 3j, alarm information is transmitted to the central monitor 4 via the network 2. The information that alarm information is transmitted is informed by, for example, displaying a warning mark and the room No. or name of the patient on the display screen of the central monitor 4. In order to cause the information to be recognized more surely, the warning mark may be displayed in a blinking manner, or a warning sound may be output.

When such an alarm is received, the medical person in the nurses' station 200 may operate the display of the central monitor 4 to check in real time the biological information of the patient from whom alarm information is generated, and the image of the camera which takes a picture of the appearance of the patient, on the display screen of the central monitor 4 via the network 2.

Since also the bedside monitors 3a, 3b, 3c, ..., 3j are connected to the network 2, also in bedside monitors other than the bedside monitor from which alarm information is transmitted, the biological information of the patient from whom alarm information is generated, and the real-time image of the camera which takes a picture of the appearance of the patient can be displayed on the display screens to be checked. In this case, the checking operation can be performed by conducting an operation on the display of the bedside monitor, for example, an operation in which, for example, a patient room, a bedside monitor, and a patient (input of the patient ID) are designated by using display buttons of the monitor.

Since the bedside monitors 3a, 3b, 3c, ..., 3j are connected to the network 2, biological information of an arbitrary patient can be displayed on the bedside monitor to which wireless communication is sent from the portable terminal 5. Also in this case, an operation may be performed in which, for example, the designation of a patient room, that of a bedside monitor, and that of a patient (input of the patient ID) are designated by using display buttons of the monitor.

Next, images to be displayed on the displaying section 44 of the receiving device (the bedside monitors 3a, 3b, 3c, ..., 3j or the central monitor 4), namely, images to be displayed on the displaying section of the bedside monitors 3a, 3b, 3c, ..., 3j or central monitor 4 which is arbitrarily designated by the medical person will be described with reference to FIGS. 3 and 4. The following description will be made assuming that, as described with reference to FIG. 1, abnormality occurs in the biological information of the patient 6j in the patient room No. 210, and alarm information is wirelessly transmitted from the bedside monitor 3j. The alarm information is received by the portable terminal 5 of the medical person A who is responsible for the patient 6j. At this time, it is assumed that the medical person A is in the vicinity of the patient 6a in the course of rounds, and in a situation where the medical person can designate the bedside monitor 3a, and transmit the alarm information to the bedside monitor 3a through the portable terminal 5 by short-range wireless communication.

Figure 3:
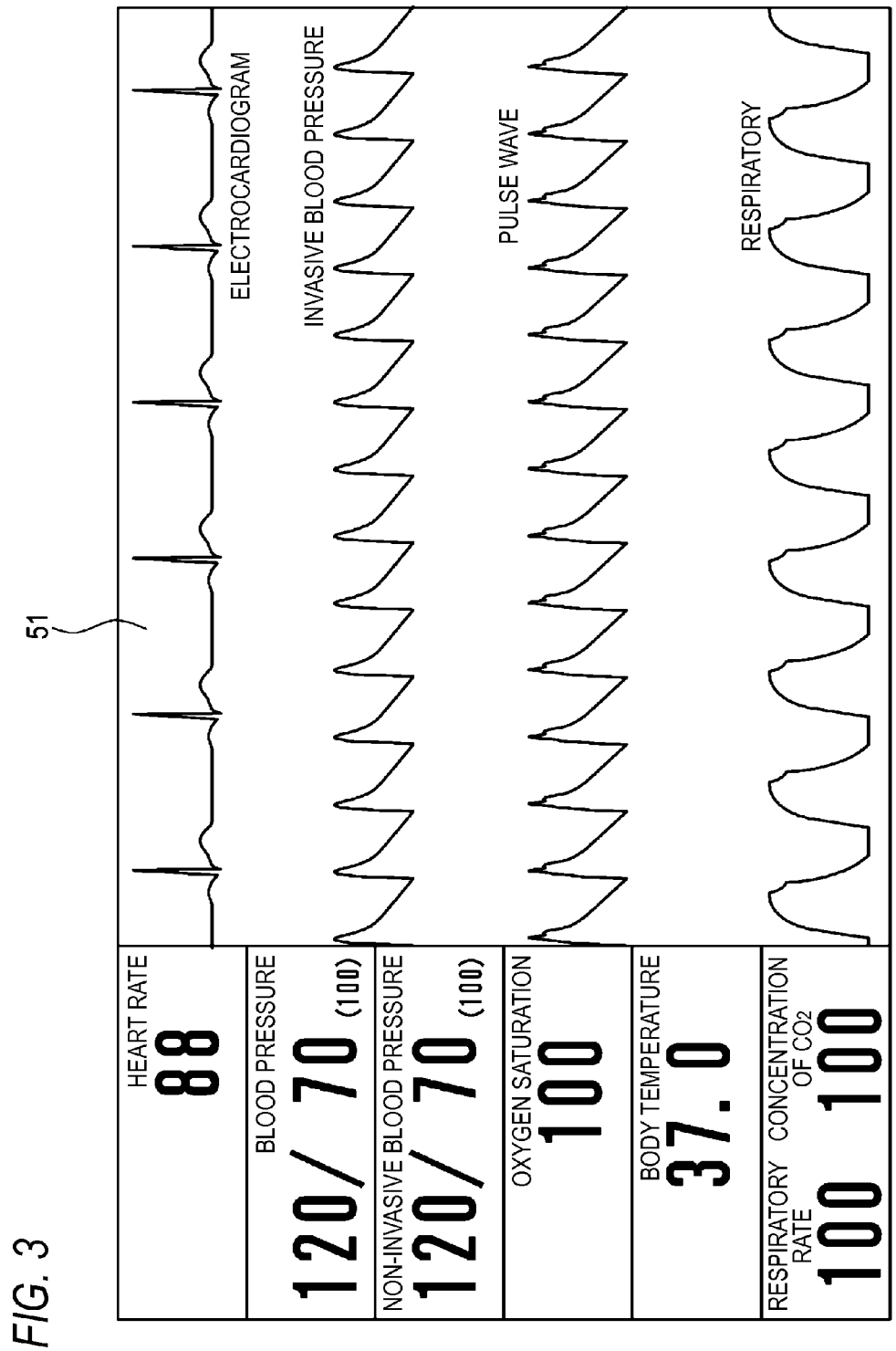
FIG. 3 is a view illustrating an example of biological information displayed on a bedside monitor.

As shown in FIG. 3, an image 51 of the biological information which is measured from the patient 6a is displayed on the bedside monitor 3a until alarm information is transmitted through the portable terminal 5. When alarm information is transmitted to the bedside monitor 3a through the portable terminal 5, an image 61 of biological information of the patient 6j from whom alarm information is generated is displayed on the bedside monitor 3a as shown in FIG. 4, the biological information being received via the network 2.

Figure 4:
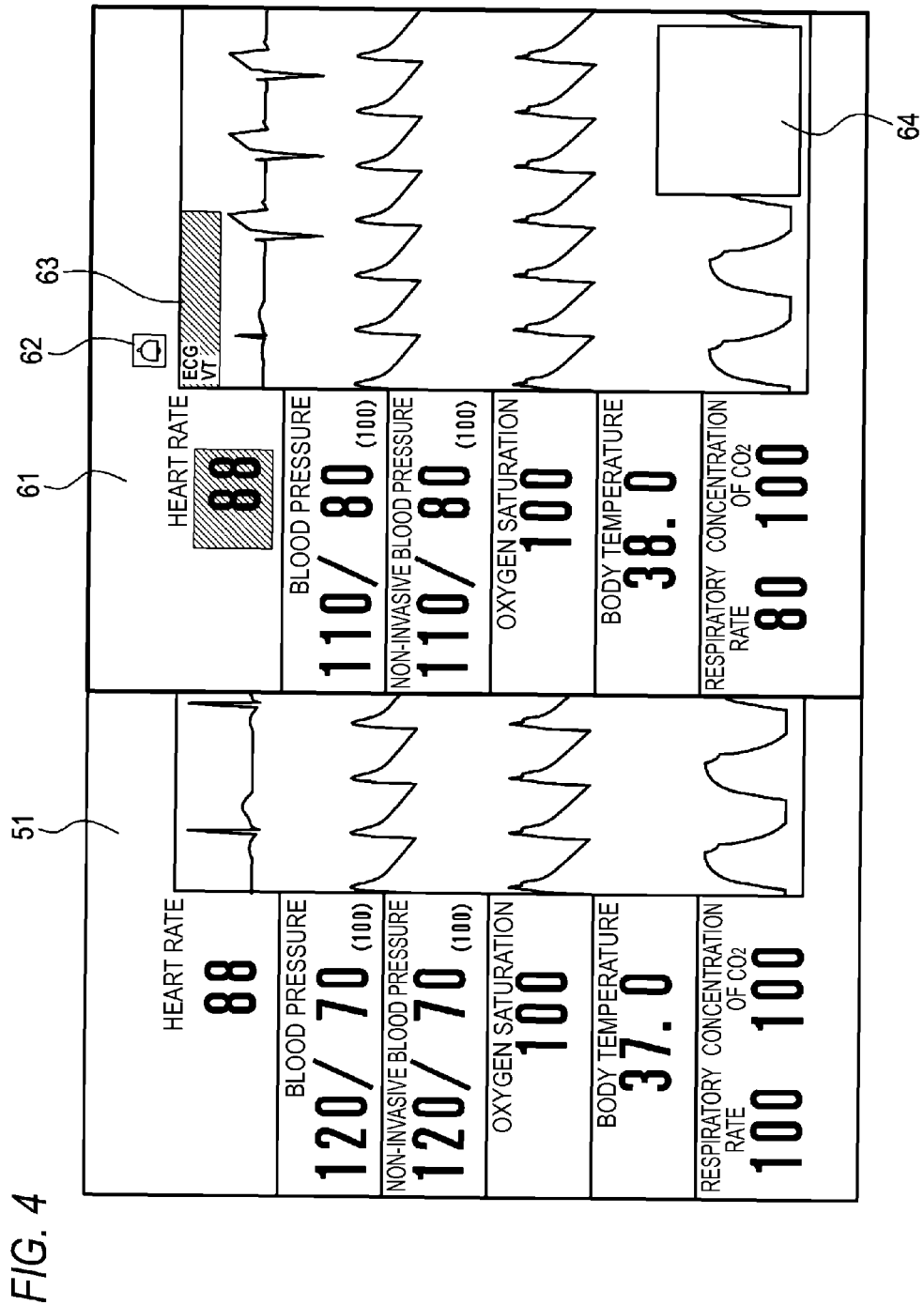
FIG. 4 is a view illustrating biological information of a patient from whom alarm information is generated, the biological information being displayed on the bedside monitor as a result of wireless transmission from a portable terminal.

As shown in FIG. 4, the image 61 of the biological information of the patient 6j from whom alarm information is generated can be displayed overlappingly with the image 51 in a part of the displaying section of the bedside monitor 3a. When the image 51 is not entirely hidden and displayed partially overlappingly in this way, also the biological information of the patient 6a which is under measurement through the bedside monitor 3a can be checked, and it is possible to respond also to a case where abnormality occurs in the biological information of the patient 6a.

A warning mark 62 informing that abnormality occurs in the patient 6j is displayed in the image 61 showing the biological information of the patient 6j. In a column 63 of warning reason, for example, a comment "ECG, VT" which indicates a symptom of ventricular tachycardia is detected in the electrocardiogram is displayed. Moreover, a real-time camera image which is formed by taking the state of the patient 6j from whom the alarm information is generated, by the camera 7j is displayed in a patient image displaying area 64.

According to the thus configured medical monitoring system 1 of the embodiment, short-range wireless communication is performed by the central monitor 4 carried by the medical person, and therefore the biological information of the patient from whom the alarm information is generated can be checked through the nearest monitor. Even when the medical person does not move to the patient room of the patient from whom alarm information is generated, the condition of the patient can be determined rapidly and correctly in the nearest place where a monitor is disposed. This can reduce the burden on the medical person. Even in the case where a plurality of alarms are generated, for example, a determination against the alarms can be performed correctly and rapidly, and the priority of a patient who must be promptly treated can be correctly determined, so that correct responses are enabled.

The signal which is to be wirelessly transmitted to the portable terminal 5 is only alarm information, and only the information is displayed on the displaying section 34. Therefore, the displaying section 34 can be suppressed to a small size, and the portable terminal 5 itself can be miniaturized. The biological information of the patient from whom the alarm information is generated can be checked by using the screen of the nearest monitor. Therefore, it is not required to enhance the size and performance of the portable terminal 5 with the purpose of displaying a plurality of sets of information of the patient from whom the alarm is generated.

Biological information of arbitrary patient can be displayed on the bedside monitor to which the wireless transmission from the portable terminal 5 is sent. Therefore, the biological information of the patient from whom the alarm information is generated, and that of another patient with the same disease can be displayed to be compared to each other, and the diagnosis and the procedure can be performed more correctly.

Moreover, the image 61 of biological information on the bedside monitor 3j from which alarm information is transmitted can be displayed overlappingly with a part of the display of the image 51 of biological information on the bedside monitor 3a to which alarm information is wirelessly transmitted from the portable terminal 5. According to the configuration, the biological information of the patient 6a which is under measurement through the bedside monitor 3a can be processed in a state where it is checkable. Even in the case where abnormality occurs in the biological information of the patient 6a, therefore, it is possible to promptly respond to the case, and surer procedures can be performed.

Moreover, the warning mark, a comment concerning the reason of the alarm, a camera image, and the like are displayed in the image showing the biological information of the patient from whom the alarm information is generated. Therefore, the medical person can make a rapid and correct determination, and apply adequate procedures. Particularly, the camera image which displays the state of the patient in real time enables a determination whether the patient is urgent, whether the alarm is caused due to technical alarm or not, or the like to be performed more rapidly.

The case where alarm information is wirelessly transmitted only from the bedside monitor 3j to the portable terminal 5 of the medical person A has been described with reference to FIG. 4. The presently disclosed subject matter is not limited to this mode. For example, the presently disclosed subject matter is applicable also in the case where alarm information is transmitted from two or more bedside monitors. In this case, the medical person A may select one of the sets of transmitted alarm information, and the selected alarm information may be transmitted to an arbitrarily bedside monitor or the like by short-range wireless communication.

Specifically, in the case where alarm information is wirelessly transmitted from the bedside monitors 3d and 3j to the portable terminal 5 of the medical person A, the medical person A can select one of the patient 6d and 6j as a patient who is to be preferentially checked. According to the configuration, only alarm information transmitted from the bedside monitor 3d for the selected patient (in this example, the patient 6d) may be transmitted by short-range wireless communication from the portable terminal 5 to the bedside monitor 3a, and the biological information of the patient 6d with a higher priority can be displayed on the displaying section of the bedside monitor 3a to be checked. According to the configuration, a patient with a higher priority can be preferentially subjected to treatment, and rapid and correct responses can be performed.

In the case where alarm information is transmitted from two or more bedside monitors, the medical person may select two or more sets of alarm information. In the specific example described above, namely, it is possible to select two sets of alarm information, i.e., the alarm information transmitted from the bedside monitor 3d, and that transmitted from the bedside monitor 3j. In the case where the two sets of alarm information are transmitted to the bedside monitor 3a by short-range wireless communication, the biological information of the patient 6d, and that of the patient 6j can be simultaneously displayed on the displaying screen of the bedside monitor 3a to be checked. In this case, the biological information of the patient 6d, and that of the patient 6j may be displayed partly overlappingly on the displaying section of the bedside monitor 3a, or the displaying section may be split, and they are displayed in the respective split displaying section. According to the configuration, in the case where the patients are equivalent in treatment emergency, the biological information of the patients can be simultaneously displayed, and rapid and correct responses can be performed.

The case where bedside monitors are disposed in one floor (for example, a surgical floor) of a hospital has been described with reference to FIG. 1. Also in the case where different departments such as surgery, internal medicine, pediatrics are arranged in different floors of a hospital, the present system can be applied as far as bedside monitors in the floors are connected to the network 2. Also in this case, the medical person is enabled to check all sets of biological information of all patients, simply by transmitting alarm information from the portable terminal 5 to the nearest monitor. Even when a medical person in charge of internal medicine is on the surgical floor, the medical person is enabled to check biological information of a patient of internal medicine from whom alarm information is generated, by transmitting alarm information to the nearest monitor (a monitor in surgery) by short-range wireless communication.

Second Embodiment

Next, a second embodiment of the presently disclosed subject matter will be described. The second embodiment in which, in addition to alarm information, biological information that is determined as abnormal (a biological information signal which exceeds a threshold) is wirelessly transmitted from a bedside monitor that detects abnormality will be described. The configuration of the medical monitoring system is identical with that (FIGS. 1 and 2) of the first embodiment, and the same reference numerals will be used.

When the portable terminal 5 receives alarm information and biological information which exceeds the threshold (hereinafter, referred to as abnormal biological information) which are wirelessly transmitted from a bedside monitor, alarm information including information indicating that abnormality occurs in the biological information of the patient, and information such as the patient ID, the patient room No., the name of the patient, and the abnormal biological information (a biological waveform of the abnormal, a measurement value of the abnormal, and the like) are displayed on the display screen of the portable terminal 5.

When the medical person then operates the portable terminal 5, the alarm information and the abnormal biological information are transmitted by short-range wireless communication to the arbitrary monitor (one of the bedside monitors 3a, 3b, 3c, . . . , 3j and the central monitor 4) which is selected by the medical person.

In the monitor which receives the alarm information and the abnormal biological information from the portable terminal 5, the received alarm information and abnormal biological information are displayed on the displaying section 44. Namely, first, the alarm information including the information indicating that abnormality occurs in the biological information of the patient, and the information such as the patient ID, the patient room No., the name of the patient, and the abnormal biological information (the biological waveform of the abnormal, the measurement value of the abnormal, and the like) are displayed on the displaying section 44.

According to the thus configured medical monitoring system, first, only the abnormal biological information is at once displayed on the larger monitor screen without the other biological information of the patient, and the contents of the displayed abnormal biological information can be checked. Therefore, the biological waveform of the abnormal, the measurement value of the abnormal, and the like can be rapidly checked, and therefore a determination on procedures can be conducted more surely.

In this case, in addition to the display of only abnormal biological information, alternatively, other information of the patient may be acquired via the network 2, and enabled to be displayed and checked. In place of the display of only abnormal biological information, namely, the biological information of the patient from whom the alarm information is generated may be displayed on the displaying section 44. Information of all parameters under measurement (information such as a waveform or a measurement value, and a camera image) may be displayed.

According to the configuration, also in the case where a clear determination cannot be made based on only biological information from which abnormality is detected, other biological information can be easily checked, and sure determination can be rapidly made. Alternatively, abnormal biological information is first caused to be rapidly displayed, by the initial short-range wireless transmission, and, during a period when a work of checking the contents of the information is performed, information having a large amount of data such as the camera image may be fetched into the monitor, and an information display and checking work in which priorities are set, and which are efficient can be performed.

With respect to the alarm information and abnormal biological information which are displayed on the displaying section 44, similarly with case which has been described with reference to FIG. 4, the two sets of information may be displayed partly overlappingly with the original image 51 in a part of the displaying section 44. Also in the case where alarm information and abnormal biological information are transmitted from two or more bedside monitors, a control which is similar to that in the first embodiment is performed.

Although the presently disclosed subject matter has been described in detail and with reference to the specific embodiments, it is obvious to those skilled in the art that various changes and modifications can be made without departing from the spirit and scope of the presently disclosed subject matter.

According to an aspect of the presently disclosed subject matter, when a medical person operates the terminal which is carried by the person and which can transmit and receive information, the medical person can check biological information of a patient from whom an alarm is generated, on a nearest monitor, and hence can determine rapidly and correctly the condition of the patient without moving to the patient. In the display of the biological information, the screen of the nearest monitor is used. Therefore, it is not necessary to increasing the size and enhancing the performance of the terminal carried by the medical person.

What is claimed is:

1. A medical monitoring system comprising:
   a plurality of biological information displaying devices which are connected to a network; and
   a portable terminal which can wirelessly communicate with the plurality of biological information displaying devices, wherein
   the plurality of biological information displaying devices includes a first device and a second device,
   biological information of a first patient is input to the first device,
   when a value of first biological information included in the biological information of the first patient is larger or smaller than a preset threshold, the first device transmits alarm information,
   the portable terminal includes: a receiving unit which can receive the alarm information from the first device; and a transmitting unit which can wirelessly transmit the received alarm information to the second device, and
   in case where the first device transmits the alarm information,
      the receiving unit of the portable terminal receives the alarm information, and the transmitting unit of the portable terminal wirelessly transmits the received alarm information to the second device, and
      when the second device receives the alarm information from the portable terminal, the second device receives the biological information of the first patient through the network and the biological information of the first patient is displayed on the second device.

2. The medical monitoring system according to claim 1, wherein
   the first device can transmit the first biological information the value of which is larger or smaller than the threshold, in addition to the alarm information, and
   in case where the first device transmits the alarm information and the first biological information,
      the receiving unit of the portable terminal receives the alarm information and the first biological information, and the transmitting unit of the portable terminal wirelessly transmits the received alarm information and the received first biological information to the second device, and
      the alarm information and the first biological information are displayed on the second device.

3. The medical monitoring system according to claim 1, wherein biological information of a second patient can be displayed on the second device.

4. The medical monitoring system according to claim 1, wherein the biological information of the first patient is displayed overlappingly with a part of an image displayed on the second device.

5. The medical monitoring system according to claim 2, wherein the alarm information and the first biological information are displayed overlappingly with a part of an image displayed on the second device.

6. A medical monitoring system comprising:
   a plurality of biological information displaying devices which are connected to a network; and
   a portable terminal which can wirelessly communicate with the plurality of biological information displaying devices, wherein
   the plurality of biological information displaying devices includes a first device and a second device,
   biological information of a first patient is input to the first device,
   when a value of first biological information included in the biological information of the first patient is larger or smaller than a preset threshold, the first device transmits alarm information,
   the portable terminal includes: a receiving unit which can receive the alarm information from the first device; and a transmitting unit which can wirelessly transmit the received alarm information to the second device, and
   in case where the first device transmits the alarm information,
      the receiving unit of the portable terminal receives the alarm information, and the transmitting unit of the portable terminal wirelessly transmits the received alarm information to the second device,
      the second device receives the biological information of the first patient through the network and the biological information of the first patient is displayed on the second device, and
   in case where the receiving unit of the portable terminal receives two or more of alarm information, the transmitting unit of the portable terminal wirelessly transmits alarm information which is selected by an operator.

7. The medical monitoring system according to claim 6, wherein, in case where two or more of alarm information are selected by the operator and the transmitting unit of the portable terminal wirelessly transmits the selected two or more of alarm information, biological information input to two or more biological information displaying devices which transmit the selected two or more of alarm information is displayed in a split manner or overlappingly with a part of an image displayed on the second device.

8. The medical monitoring system according to claim 1, wherein the second device receives the biological information of the first patient through the network based on the alarm information.

9. The medical monitoring system according to claim 6, wherein
   the first device can transmit the first biological information the value of which is larger or smaller than the threshold, in addition to the alarm information, and
   in case where the first device transmits the alarm information and the first biological information,
      the receiving unit of the portable terminal receives the alarm information and the first biological information, and the transmitting unit of the portable terminal wirelessly transmits the received alarm information and the received first biological information to the second device, and
      the alarm information and the first biological information are displayed on the second device.

10. The medical monitoring system according to claim 6, wherein biological information of a second patient can be displayed on the second device.

11. The medical monitoring system according to claim 6, wherein the biological information of the first patient is displayed overlappingly with a part of an image displayed on the second device.

12. The medical monitoring system according to claim 9, wherein the alarm information and the first biological information are displayed overlappingly with a part of an image displayed on the second device.

13. The medical monitoring system according to claim 6, wherein the second device receives the biological information of the first patient through the network based on the alarm information.

\* \* \* \* \*